US005479815A

United States Patent [19]
White et al.

[11] Patent Number: 5,479,815
[45] Date of Patent: Jan. 2, 1996

[54] METHOD AND APPARATUS FOR MEASURING VOLATILES RELEASED FROM FOOD PRODUCTS

[75] Inventors: James D. White, Hanover Park; William R. Croasmun, Glenview; Jane V. Leland, Grayslake, all of Ill.

[73] Assignee: Kraft Foods, Inc., Northfield, Ill.

[21] Appl. No.: 201,254

[22] Filed: Feb. 24, 1994

[51] Int. Cl.$^6$ ............................. G01N 31/00; G01N 33/16
[52] U.S. Cl. ............................................. 73/23.3; 128/719
[58] Field of Search ..................... 73/23.3, 23.35, 73/23.34

[56] References Cited

U.S. PATENT DOCUMENTS

| | | | |
|---|---|---|---|
| 3,398,505 | 8/1968 | Llewellyn | 73/23.35 |
| 3,451,255 | 6/1969 | Neville et al. | 73/23.35 |
| 3,622,278 | 11/1971 | Elzinga et al. | 23/232 R |
| 3,649,199 | 3/1972 | Littlejohn | 23/230 |
| 3,759,249 | 9/1973 | Fletcher et al. | 128/2.08 |
| 4,133,640 | 1/1979 | Clinton et al. | 23/230 PC |
| 4,167,667 | 9/1979 | Hall et al. | 250/288 |
| 4,178,919 | 12/1979 | Hall | 128/719 |
| 4,346,584 | 8/1982 | Boehringer | 73/23.3 |
| 4,485,822 | 12/1984 | O'Connor et al. | 128/719 |
| 4,539,209 | 9/1985 | Wilson et al. | 426/3 |
| 4,554,820 | 11/1985 | Litman | 73/23 |
| 4,772,559 | 9/1988 | Preti et al. | 436/64 |
| 4,850,371 | 7/1989 | Broadhurst et al. | 128/719 |
| 4,982,089 | 1/1991 | Johnson | 250/304 |
| 5,004,595 | 4/1991 | Cherukuri et al. | 424/48 |
| 5,042,501 | 8/1991 | Kenney et al. | 128/719 |
| 5,177,994 | 1/1993 | Moriizumi et al. | 73/23.34 |
| 5,284,054 | 2/1994 | Loebach | 73/23.3 |

FOREIGN PATENT DOCUMENTS

| 1080995 | 8/1967 | United Kingdom | 73/23.30 |
|---|---|---|---|

OTHER PUBLICATIONS

Heath and Reineccius "Flavor and Its Study" *Flavor Chemistry and Technology,* (Connecticut: AVI 1976).

Overbosch, Afterof and Haring "Flavor Release in the Mouth" *Food Review International,* vol. 7, pp. 137–184 (Marcel Dekker, 1991).

A. J. Taylor and R. S. T. Linforth "Methodology for Measuring Volatile Profiles in the Mouth and Nose During Eating," *Trends in Flavour Research,* H. Maarse and D. G. Van der Heij (Eds.) (1994).

S. M. Van Ruth, J. P. Roozen, J. L. Cozijnsen "Comparison in Dynamic Headspace Mouth Model Systems for Flavour Release from Rehydrated Bell Pepper Cuttings," *Trends in Flavour Rresearch,* H. Maarse and D. G. Van der Heij (Eds.) (1994).

P. H. Punter and A. J. Taylor, "Report of the Workshop 'Flavor Release'", *Trends in Flavour Research,* H. Maarse and D. G. Van der Heij (Eds.) (1994).

R. Linforth, I. Savary and A. J. Taylor, "Profile of Tomato Volatiles During Eating," *Trends in Flavour Research,* H. Maarse and D. G. Van der Heij (Eds.) (1994).

(List continued on next page.)

*Primary Examiner*—Hezron E. Williams
*Assistant Examiner*—J. David Wiggins
*Attorney, Agent, or Firm*—Fitch, Even, Tabin & Flannery

[57] ABSTRACT

The invention provides a method and apparatus for efficiently measuring and analyzing volatile and relatively non-volatile flavor components released during oral processing of food or other products. The subject exhales a breath sample into one or more temperature-controlled collection chambers, preferably at predetermined time intervals during the oral processing of the product. Each breath sample is then purged from its collection chamber with a non-reactive gas flow into an adsorbent, absorbent or other trap containing an interface that separates and collects the volatile and relatively non-volatile components from the breath sample. The trap is then transferred to a thermal desorber to release the volatile and relatively non-volatile flavor components from the interface surface into a measuring and analysis apparatus.

26 Claims, 6 Drawing Sheets

OTHER PUBLICATIONS

W. J. Soeting and J. Heidema, "A Mass Spectrometric Method for Measuring Flavor Concentration/Time Profiles in Human Breath," *Chemical Senses*, vol. 13, No. 4, pp. 607–617, (1988).

L. Kovacs & P. Haaz, Budapest/H., "An Approach to the Assessment of In Vivo Lipid Peroxidation by Measurement of Exhaled Pentane—, A New, Simple Instrument for Breath Pentane Analysis," *Fat Science Technology*, 93 Jahrgang Nr. 11, (1991).

Kate E. Ingham, Rob S. T. Linforth & Andrew J. Taylor, "The Effect of Eating on Aroma Release from Mint–Flavored Sweets," taken from *Flavor and Fragrance Journal*, vol. 10, pp. 15–24 (1995).

METHOD AND APPARATUS FOR MEASURING VOLATILES RELEASED FROM FOOD PRODUCTS

FIELD OF THE INVENTION

The present invention generally relates to the collection and measurement of volatile and relatively non-volatile components released into the breath of a subject by food products and other products that are orally processed by chewing or by other means.

BACKGROUND OF THE INVENTION

In the development of food products for humans, medicines and other products that are orally ingested by humans and animals, the flavor of the products is often the focus of considerable testing and analysis. A product's flavor is in large part determined by the diverse mixture of volatile and relatively non-volatile chemical components released into the mouth and nose of a subject during chewing and oral processing of the product. See Heath and Reineccius "Flavor and Its Study", *Flavor Chemistry and Technology*, (Connecticut:AVI 1986).

By analyzing the volatile and relatively non-volatile components released from food and other products during oral processing, it is possible to identify the components that contribute to desirable flavors, as well as those components that produce undesirable flavors. Moreover, if such an analysis is conducted over a period of time, then it is possible to determine the release rate of both those desirable and undesirable flavor components throughout oral processing, as well as during an "after taste" period following ingestion of the product. Volatile and relatively non-volatile flavor components are released into the vapor phase so that they circulate throughout the subject's mouth and nose. The release of these components is controlled by highly variable and complex interactions between individual flavor components and the food matrix, as well as a number of oral factors such as chewing, saliva, etc. See Overbosch, Afterof and Haring, "Flavor Release in the Mouth", *Food Review International*, 7(2), 137–184 (Marcel Dekker 1991). Because these interactions are difficult to predict, it is often necessary to identify and measure the volatile and relatively non-volatile components actually released by a food product, or other products, into a subject's oral cavity or mouth headspace. This is particularly true during the development of reduced fat or reduced calorie substitutes for full-fat or full-calorie food products.

In such products, the amounts of the flavor components released by the products and their release rates during oral processing have a large effect on the products' perceived overall flavor. The relative amounts of each released volatile and relatively non-volatile flavor component, which vary over time, actually dictate the products' perceived flavor. The relative release rate of each volatile and relatively non-volatile component also affects the "staying power" of that perceived flavor. As mentioned above, the release rate of flavor components may be affected by the food product matrix and the manner in which the product is orally processed, i.e. by chewing and circulation of liquid and semi-liquid components in the subject's mouth. Hence, it is often desirable to study both the relative amounts and the release rate of particular flavor components during oral processing over a predetermined time period.

Data on the identity, relative amounts and release rates of volatile and relatively non-volatile components may be used to increase or decrease the amount of certain volatile and relatively non-volatile components in the product, as well as to adjust elements of the food matrix itself. This may include changes in the product recipe or formulation, or changes in the preparation steps for the product. The data may also be used to tailor the flavor of a product for a specific purpose or for a specific audience. The data further may be used to determine changes in released flavor components caused by alterations in the preparation or processing of a product for cost efficiency or other reasons.

Common methods used to analyze volatile and relatively non-volatile flavor components in foods were designed primarily to quantify the total amounts of flavor components in the products before oral processing. Such methods, however, typically did not measure the amount of volatile or relatively non-volatile flavor components actually released from food products into the mouth headspace and nose of a subject during oral processing, nor were they adapted to study the release rates of those components.

Similarly, common approaches for measuring the content of breath samples were not well suited for the study of flavor components in foods and other orally ingested products. See e.g., Soeting and Heidema, *Chemical Senses*, 13, 607 (1988). One system included a mouthpiece and a tube for carrying the exhaled breath of the subject into a mixing chamber. A sample outlet and exit tube connected the mixing chamber to a measuring device, such as a mass spectrometer. In addition, heat was applied to the system to prevent condensation of moisture from the breath sample on the system components. The mixing chamber insured that the exhaled breath sample mixed with previous samples, and that a small quantity of the combined breath sample was drawn from the chamber into the measuring device. Such approaches were for use in clinical toxicology, occupational medicine and exercise physiology studies.

Another approach used a pumping system to draw an air sample from the nose of a subject, through a glass nosepiece and past a membrane separator fitted to a quadrapole mass spectrometer. In that approach, the subjects also manipulated the sample in their mouth. Other systems have used a solid state sensor adapted to measure one component from a breath sample, such as pentane. In that type of system, a carrier gas and a breath sample were injected into a separating column and were then circulated toward a solid state sensor.

Those prior systems generally required continuous respiration by the subject into tubes or interfaces. Certain of these approaches, in addition, did not provide for sampling components from the mouth headspace. Some systems, in fact, were designed to exclude "dead air" from the mouth, throat, nasal passages and bronchial tubes of a subject.

More importantly, the prior approaches were intended to generally study a single gas such as oxygen or carbon dioxide or only a single component in a breath sample. In approaches using a mass spectrometer, it was possible to measure more than one ion and thus more than one compound at a time, but the sensitivity of the resulting measurements was reduced. Most prior approaches also were not designed to measure a range of volatile and relatively non-volatile components released into the mouth headspace and nose of a subject during oral processing of a food or similar product. Moreover, in some prior applications, the systems did not collect sufficient amounts of the volatile components to accurately measure flavor components released in very small quantities.

The present invention provides a method and apparatus that will measure and analyze both volatile and relatively non-volatile components released from food or other products during oral processing. The method of the invention efficiently collects breath samples from a subject at predetermined time intervals so that the nature and amounts of flavor components actually released by a product during oral processing can be determined. Moreover, the method of the invention does not require continuous sampling, but permits the storage of samples for a limited period so that they can be studied later at the user's convenience.

The method of the invention, in addition, can be used to measure components that are present in small concentrations, yet are important to the flavor of a product. The method is also well suited for measuring a variety of different classes of flavor compounds that may be released by a given product. The invention, further, is cost effective and requires only a limited amount of custom designed equipment.

SUMMARY OF THE INVENTION

One object of the invention is to provide a method and apparatus for efficiently measuring and analyzing volatile and relatively non-volatile flavor components released during oral processing of food or other products by a subject.

Another object of the invention is to provide a method and apparatus for efficiently measuring and analyzing more than one volatile or relatively non-volatile component released during oral processing of food or other such products by a subject.

Another object of the invention is to provide a method and apparatus for measuring and analyzing the volatile and relatively non-volatile components released by food or other such products by a subject in a series of breath samples, over a period of time.

Further and additional objects will be apparent from the following description, drawings and claims.

In one embodiment, a subject is provided with an amount of a food or other product for oral processing, e.g., chewing the product, circulating the product through the subject's mouth or otherwise orally preparing the product for ingestion. This oral processing is preferably conducted while the subject's mouth and nose are closed, sealed or partially sealed.

The subject then exhales a breath sample into one or more collection chambers that are preferably maintained in a temperature controlled cabinet to prevent condensation of portions of the sample. Each sample preferably is collected from the subject's mouth rather than from the nose to obtain a maximum concentration of volatile and relatively non-volatile components released by the product. To study the release rates of certain components, multiple breath samples are preferably collected from the subject in separate chambers at predetermined time intervals during the oral processing of the product.

Each breath sample is then purged from its collection chamber with a non-reactive gas flow into a trap containing an interface that separates and collects the volatile and relatively non-volatile components from the breath sample. This interface preferably is an inert adsorbent material selected for its ability to collect volatile or relatively non-volatile components likely to be released by the product. A substrate coated with an absorbent or other material capable of collecting volatile and relatively non-volatile components may also be used. The interface, in addition, preferably permits any moisture contained in the breath sample to pass through the trap, leaving only the collected volatile and relatively non-volatile components on the interface.

The adsorbent trap is then transferred to a thermal desorber or other device capable of releasing the adsorbed volatile and relatively non-volatile flavor components from the interface surface into a measuring and analysis apparatus. In one embodiment, volatile and relatively non-volatile components collected by an adsorptive trap are thermally desorbed from the trap and flushed into a gas chromatograph by a non-reactive gas flow. There, the components are physically separated on the chromatographic column and arrive at a detector at different times. The results obtained from the gas chromatograph may be used to determine the quantity and, in some instances, the identity of the various components. The gas chromatograph may also supply each component fraction to spectroscopic or other analysis devices, such as a quadrapole mass spectrometer, an ion trap detector, an infra-red spectrometer, an atomic emission detector or other devices capable of analyzing and characterizing the component fraction.

In another embodiment, the subject blows each breath sample first through a condensation trap and then into the collection chamber. The condensation trap captures relatively non-volatile flavor components that might not otherwise be recovered from the collection chamber or could not be readily desorbed from an adsorbent trap. The condensation trap preferably includes non-reactive glass tubing packed with a non-reactive and non-adsorbent substrate, such as glass wool. Other materials may be used provided that the materials withstand high temperatures and do not react with flavor compounds. The trap is maintained at a temperature that will encourage the condensation on the substrate of slightly volatile or relatively non-volatile flavor components in the subject's breath and permits the volatile components to pass through into the collection chamber.

The condensation trap is then heated to revaporize the condensed components, so that they may be purged into measuring and analysis devices such as a gas chromatograph and mass measuring device. Similarly, the flavor components that passed through the condensation trap into the collection chamber also may be flushed into an adsorbent trap so that they may be studied as discussed above.

BRIEF DESCRIPTION OF THE DRAWINGS

For a more complete understanding of the invention, reference should be made to the embodiments illustrated in greater detail in the accompanying drawings and described below by way of examples of the invention. In the drawings.

It should be understood that the drawings are not necessarily to scale. In certain instances, details for the actual structure which are not necessary for the understanding of the invention have been omitted. It should be understood, of course, that the invention is not necessarily limited to the particular embodiment illustrated herein.

DETAILED DESCRIPTION OF THE INVENTION

Figure 1:
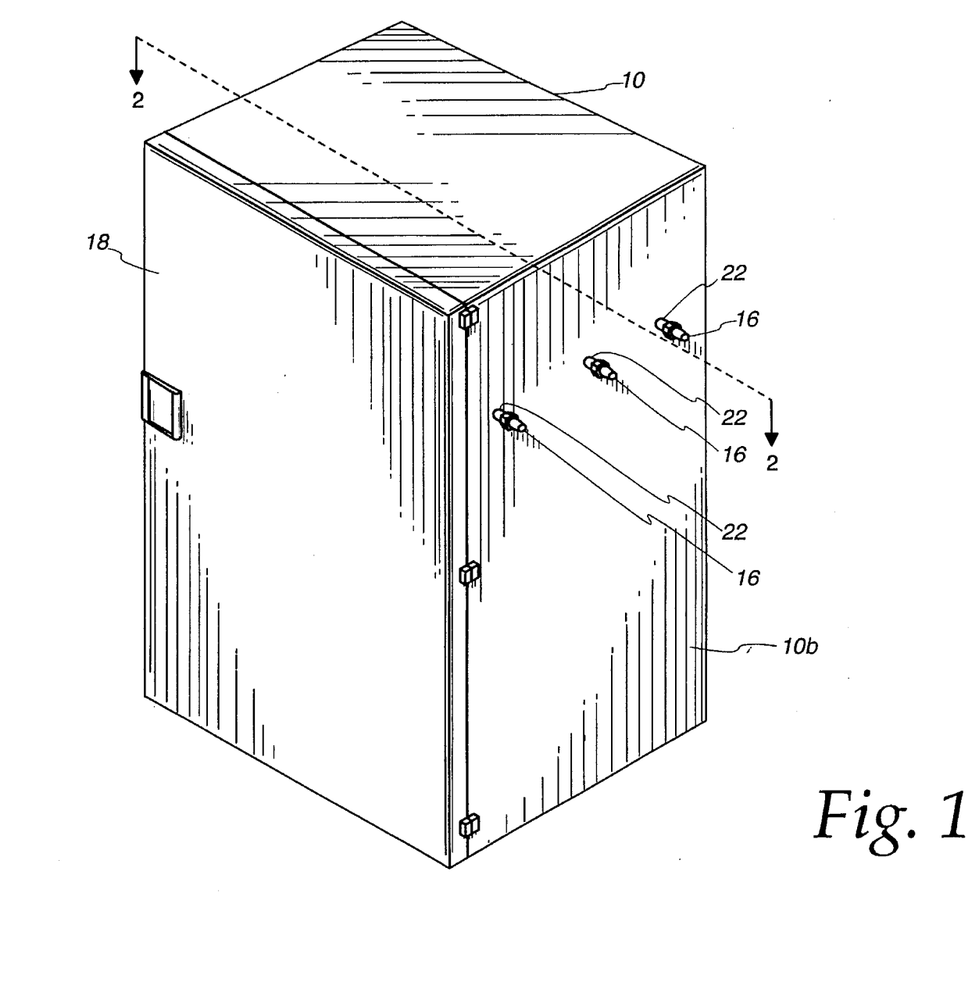
FIG. 1 is a perspective view of a temperature controlled cabinet containing three collection chambers, prepared to receive breath samples from a subject.
Figure 2:
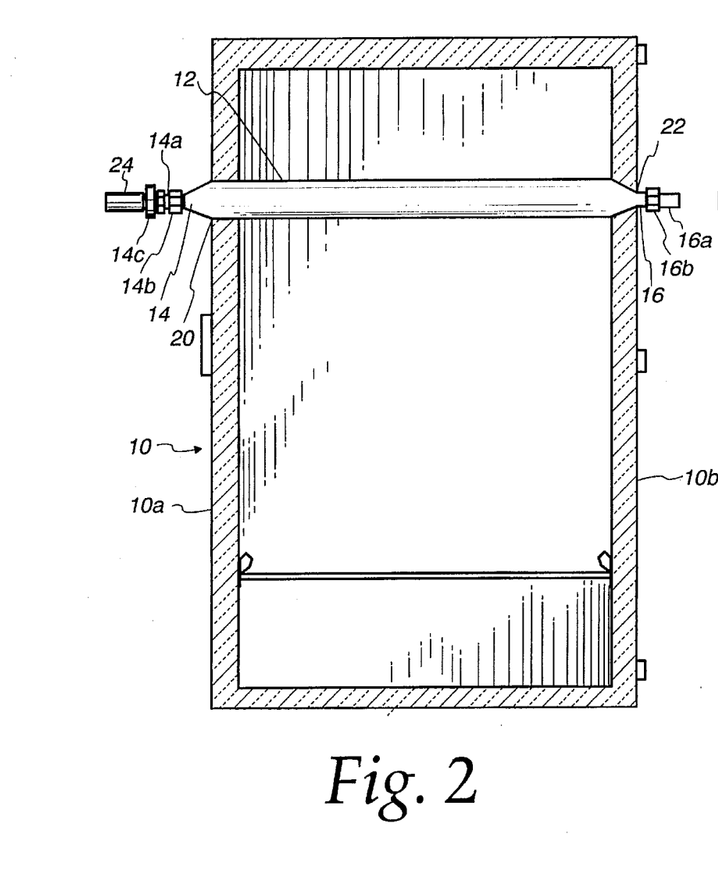
FIG. 2 is a sectional view through line 2—2, of FIG. 1 illustrating the cabinet and collection chambers.

Referring now to the drawings, and more particularly to FIGS. 1 and 2, one embodiment of the invention includes a temperature controlled cabinet 10 containing one or more generally cylindrical collection chambers 12. In this embodiment, the cabinet 10 is provided with three collection chambers 12 to study release rates of flavor components, although the number of collection chambers 12 may be increased or decreased depending on the number of breath samples required. Each collection chamber 12 normally includes a generally tubular entrance conduit 14 and a generally tubular exit conduit 16. Depending on the equipment and application, the entrance conduit. 14 and exit conduit 16 may be reversed for a particular collection chamber 12.

The cabinet 10 may be an oven or another such device capable of holding and maintaining the collection chambers 12 at a preselected temperature, typically in the range of about 85° C. to 175° C. and preferably about 125° C. The holding temperature may also be increased or decreased depending on the application. In the preferred embodiment, the cabinet 10 is a Blue M oven, model No. OV-490A-2, (Blue M Electric Company, Blue Island, Ill.) with right and left side walls 10a and 10b, although other suitable temperature controlled ovens or cabinets may be used.

The cabinet 10 further is typically provided with a latched, hinged door 18 providing access to the interior of the cabinet 10. In addition, the cabinet side walls 10a and 10b are preferably provided with opposing first ports 20 and second ports 22. These ports 20 and 22 are disposed to allow access to all or a part of the collection chamber entrance conduits 14 and exit conduits 16, respectively, from the exterior of the cabinet 10. Thus, in the embodiment of FIGS. 1–3 the cabinet's left side wall 10a is provided with three evenly spaced first ports 20 and the right side wall 10b is provided with three second ports 22 to accommodate the three collection chambers. The first port 20 and second port 22 may also be reversed, if desirable, for a particular study.

Figure 3:
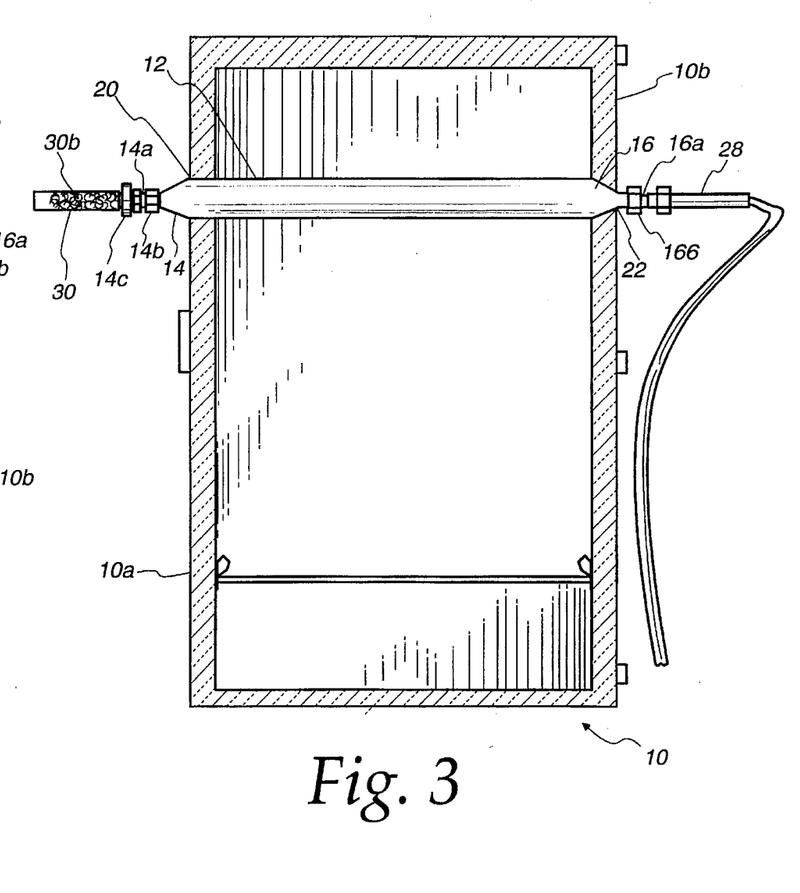
FIG. 3 is a sectional view through line 2—2 of FIG. 1 of the cabinet and collection chambers, with adsorbent trap and purge line attached.

In the preferred embodiment, the diameter of each second port 22 is sized and positioned to receive and provide support to at least the exit conduit 16 of each collection chamber 12. The diameter of each first port 20 is preferably somewhat larger than the outer diameter of the collection chambers 12 so that the chambers 12 may be inserted through the first ports 20 into the interior of the cabinet 10 without opening the cabinet door 18. In addition, the first ports 20 are positioned so that they may support at least the entrance conduits 14, if not the main body of the collection chambers 12.

Each collection chamber 12 is preferably constructed of glass or other non-reactive materials. As mentioned above, the axial length of the chanters is preferably sufficient to ensure that at least a portion of the entrance conduit 14 and exit conduit 16 protrude through the entrance 20 and exit 22 ports of the cabinet 10, while most of the main body of the chamber 12 is maintained within the cabinet 10. Also as mentioned above, the chambers 12 are preferably cylindrical, but other geometries may also be used.

The volume of each collection chamber 12 preferably is sufficiently large to hold a representative breath sample, with a minimum sample loss due to the displacement of air from within the collection chamber 12. In the preferred embodiment, the main body of each collection chamber 12 has an outer diameter of about 1.25 inches (3.18 centimeters) and a volume of about 380–400 milliliters. This volume was about two to five times the volume of a breath sample exhaled by a human subject at about 400–500 milliliters per minute for about 10–20 seconds. The volume of the collection chambers 12, of course, may be varied depending on factors such as the specific application of the invention, the exhalation volume of the subject, and the specific construction of the collection chamber.

In addition, the chamber entrance conduits 14 and exit conduits 16 are preferably sized to permit a subject to flow a breath sample through the entrance conduit 14 without undue resistance from back pressure caused by compression of ambient air within the chambers 12. Rather, the air previously contained within the chamber 12 is preferably easily exhausted from the interior of the collection chamber 12 through the exit conduit 16. In the one embodiment, both the entrance conduit 14 and exit conduit 16 have an outer diameter of about 0.25 inch (0.64 centimeter) to allow the passage of a breath sample from a subject into the chamber 12 without undue effort.

The entrance conduit 14 and exit conduit 16 also include stem portions 14a and 16a, respectively, that preferably extend past the outer walls of the cabinet 10 for about 1 inch (2.54 centimeters). In addition, connectors may be added to the entrance stems 14a and exit stems 16a to permit the easy connection of hoses and traps to the collection chambers 12 as discussed below. In one embodiment, a 0.25 inch (0.64 centimeter) Swagelok union 14b was installed on the entrance stem 14a and a 0.25 inch (0.64 centimeter) to 0.125 inch (0.318 centimeter) Swagelok reducing union 16b was installed on the exit stem 16a.

Typically, the entrance conduits 14 and exit conduits 16 are uncovered to permit equalization of the ambient air pressure and the air pressure within the collection chambers 12. However, should environmental or test conditions require, the entrance conduits 14 may be sealed with removable closures, one-way valves of an appropriate non-contaminating material, or other devices for periodically opening and closing the entrance conduit 14. Similarly, the other exit conduits 16 may also be sealed with such closures, valves or devices to allow the escape of air from the collection chambers 12 when a subject flows breath samples into the collection chambers 12.

To aid in introducing a breath sample into each collection chamber 12, mouthpieces 24 may be connected to the stem 14a of the entrance conduit at the union 14b. This mouthpiece 24 typically is a relatively short length of non-reactive glass or plastic tubing. In the preferred embodiment, the mouthpiece 24 includes a section of glass tubing about 0.75 inches (1.91 centimeters) long with an outer diameter of about 0.25 inch (0.64 centimeter). The mouthpiece 24 preferably is connected to the stem 14a using a 0.25 inch (0.64 centimeter) thumbwheel nut and Teflon ferrule 14c. All or a portion of the glass tubing is covered with a length of plastic or rubber tubing, such as Tygon tubing, or a similar material to protect the subject's lips.

The mouthpieces 24 normally are of a limited length to prevent condensation of components in the breath sample on the mouthpiece. However, when conditions require, an extended-length mouthpiece may be used. The mouthpieces 24 may be heated to prevent condensation, and may be of other sizes, configurations or dimensions as determined by the nature of the subject, the particular apparatus available and the nature of the product to be analyzed.

Similarly, a flow meter (not shown) may be attached to the exit stem 16a in order to monitor the displacement of air from the collection chamber 12 by the subject and to monitor and standardize the size of the breath sample. Such flow meters are generally available to those skilled in the art.

Alternatively, a simple device for controlling exhaled volume was constructed from a toy "punching balloon" and a hose clamp. The hose clamp attaches the distal end of the balloon to the exit stem 16a of collection chamber 12 such that the balloon could be inflated to a volume of about 170–250 milliliters without creating significant back pressure in the collection chamber 12. The opening of the balloon was provided with a one way valve, which was connected to the exit stem 16a of a collection chamber 12, to prevent back flow of air from the balloon into the collection chamber 12.

As shown in FIG. 3, once a breath sample is collected, the mouthpiece 24 (shown in FIG. 2) is disconnected from the entrance union 14b and an adsorbent trap 30 is preferably connected to the entrance union 14b, the thumbwheel nut and Teflon ferrule 14c. A source for non-reactive gas 28 is connected to the exit union 16b of the collection chamber 12. The preferred non-reactive gas is helium, but other non-reactive gases may be used. Alternatively, the gas source 28 may be connected to the entrance union 14b, and the adsorbent trap may be connected to the exit union 16b using suitable fittings.

Such adsorbent traps 30 are well known in the art, and commonly include a substrate 30b arranged within a length of glass or metal tubing, or some other such chamber. The substrate 30b is typically made of an adsorbent material including porous polymers such as those supplied under the tradename Tenax-TA by Chrompack, Inc., or is coated with adsorbent materials. Alternatively, the substrate may be provided with a layer or coating of an absorbent material.

The substrate 30b is disposed so that air and mixtures of gases may flow through the substrate 30b and exit trap 30 into another chamber or into the atmosphere. The specific adsorbent or absorbent material and substrate configuration used will depend on the particular application and the components to be analyzed and measured.

The preferred adsorbent trap 30 is supplied by Chrompack Inc., N.J., and is packed with about 90–100 milligrams of an adsorbent material supplied under the tradename Tenax-TA by Chrompack, Inc. This is considered a general purpose adsorbent trap and typically captures most, if not all, volatile and relatively non-volatile components in a breath sample while allowing most water vapor in the sample to pass through the trap. Other adsorbent traps that are more or less effective for collecting certain types of components may also be used depending on the products under study and the components released by those products during oral processing.

Once the adsorbent trap 30 and gas source 28 are attached to the collection chamber 12, sufficient pressure is supplied through the exit conduit 16 by the non-reactive gas source 28 to purge the breath sample from the collection chamber 12, through the entrance conduit 14 and into the adsorbent trap 30. This permits the collection of volatile and relatively non-volatile components in the breath sample on the adsorbent trap 30 for subsequent study. As mentioned above, the adsorbent trap 30 preferably does not collect significant amounts of the moisture usually included in a breath sample. Such moisture may interfere with the analysis and measurement of flavor components and often is removed with specially adapted techniques or equipment.

In most instances, each collection chamber 12 will be provided with a separate adsorbent trap 30. This permits the separate analysis of the amount and nature of volatile and relatively non-volatile components obtained in each collection chamber 12. In some instances, it may be desirable to use a single adsorbent trap 30 for more than one chamber 12, or multiple traps 30 for a single chamber 12.

Figures 4, 5:
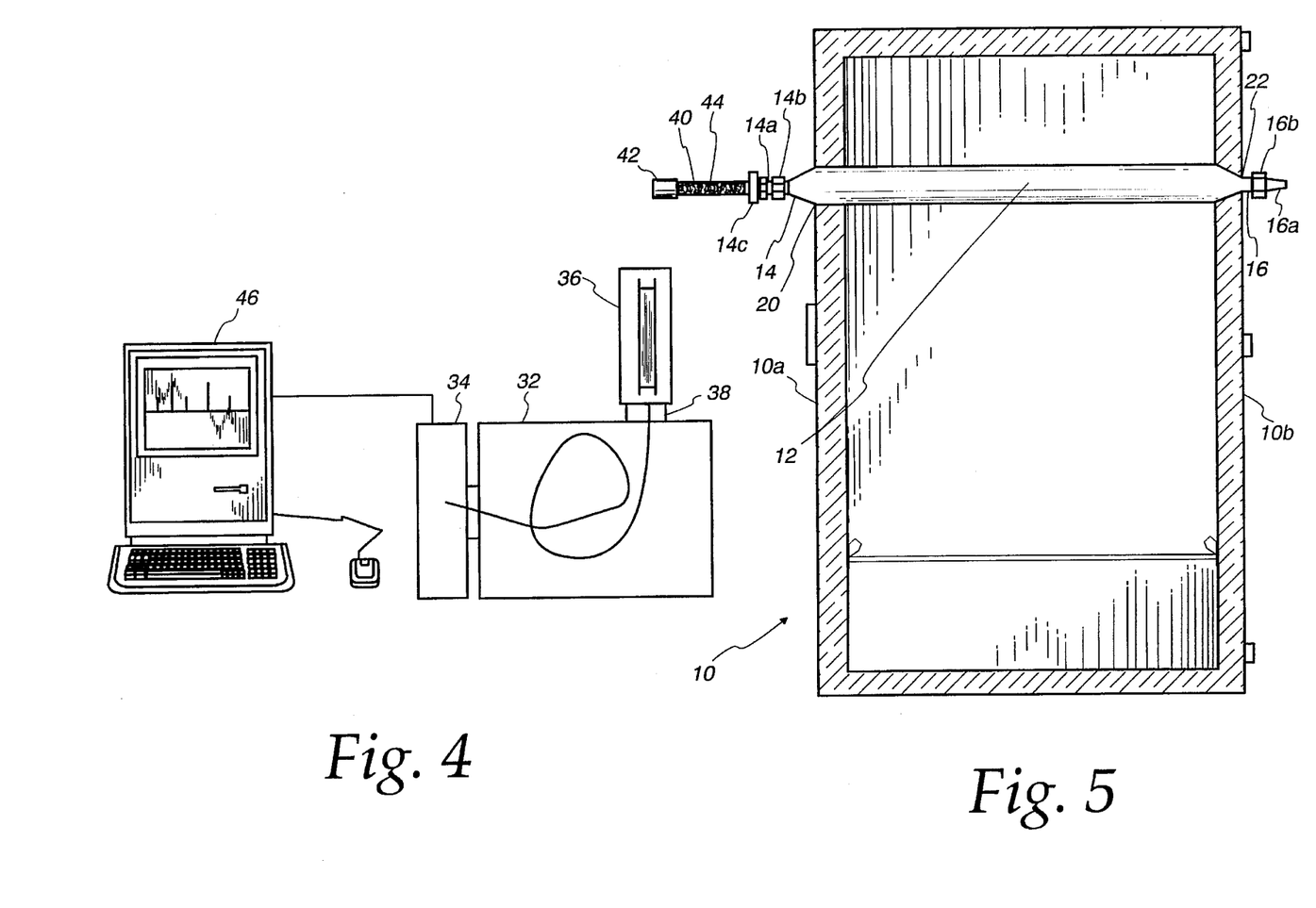
FIG. 4 is a schematic of a gas chromatograph and mass measuring device and data analysis apparatus.
FIG. 5 is a sectional view through line 2—2 of FIG. 1 of the cabinet and collection chambers with the optional condensation trap attached.

Each adsorbent trap 30 is disconnected from the entrance union portion 14b for analysis and measurement of the adsorbed contents of the trap 30. A variety of devices and methods may be used to analyze and measure the contents of the adsorbent trap 30, including a gas chromatograph 32 and mass analysis device 34. In the preferred embodiment, the adsorbent trap 30 is placed in a thermal desorber 36 connected by a coupler 38 to the gas chromatograph 32. The flavor components captured by the adsorbent trap 30 are flushed into the gas chromatograph 32 and then passed into the mass analysis device 34. When appropriate, other separation or analysis methods also may be used such as infrared spectroscopy and atomic emission analysis, and liquid chromatography.

In the preferred embodiment, the thermal desorber 36 is a Chrompack purge and trap injector, which includes a liquid nitrogen cold trap which can be maintained at temperatures of about −140° C., in order to trap volatiles as they are thermally desorbed from the adsorbent trap 30. The adsorbent trap 30 is placed into the desorber 36 and is heated to a temperature, preferably about 220° C., that revaporizes the volatile and relatively non-volatile components adsorbed on the trap 30. A flow of non-reactive gas, preferably helium at a flow rate of about 15 milliliters per minute, is passed through the desorber 36 for a period of time, preferably about 12 minutes, to elute the gaseous volatile and relatively non-volatile components into the cold trap of the desorber 36. The liquid nitrogen flow to the cold trap of the desorber 36 is then shut off and the cold trap is ballistically heated to about 180° C. to quickly transfer the volatile and relatively non-volatile components through the coupler 38 and into the gas chromatograph 32 for measurement and analysis.

Of course, other means for releasing the adsorbed components from the adsorbent trap 30 known to those skilled in the art may also be used. In addition, the type and arrangement of measuring and analysis apparatus will depend on the components under study and the particular needs of the evaluation procedure used.

In one embodiment, the gas chromatograph 32 is typically used to isolate, and sometimes identify based on residence time in the chromatographic column, the various volatile and relatively non-volatile components collected on the adsorbent trap 30. Such data, including particular residence times of fractions, may provide further information on the nature and amount of a particular component or fraction of a component collected on the adsorbent trap 30.

In the preferred embodiment, the gas chromatograph 32 is a Hewlett-Packard Model 5890 gas chromatograph with a SGE 30 meter DB-5 fused silica capillary column having a 0.25 millimeter inner diameter. Other chromatographs and chromatographic columns may also be used, such as a Varian 3400 gas chromatograph with a 25 meter by 0.2 millimeter ID DB-1 capillary column with a 0.5 micron film. A typical temperature program used for the Hewlett-Packard Model 5890 gas chromatograph was as follows: 40° C. initial temperature (hold 3 minutes), then 4° C. per minute to 140° C. (no hold), then 6° C. per minute to 220° C. (hold 10 minutes). The exit end of the column may be inserted directly into the source of the mass analysis device 34 or into another suitable spectrometric device.

In the preferred embodiment, the mass analysis device 34 is a Hewlett-Packard Model 5971A quadrapole Mass Spectrometer or a Finnigan ITS40 Ion Trap Detector. Such a mass analysis device 34 may be used to scan a mass range for information on the identity and quantity of unknown components in the sample or may scan for components which have common structural features. In addition, in conjunction with the gas chromatograph 32, the mass analysis device may be used to monitor several specific target components in a single analysis based on their elution times and mass spectra. Similarly, the mass analysis device 34 may be targeted for specific components present in extremely small amounts and which elute from the gas chromatograph column at established intervals. In some instances, this approach will allow detection of specific flavor components at concentrations in the product of as low as one part per billion. Other analysis methods, such as those mentioned above, may also be used for those purposes where appropriate.

As mentioned above and indicated in FIG. 4, the gas chromatograph 32 and mass analysis device 34 are preferably arranged in series, so that as components from a breath sample are eluted off the gas chromatographic column 32, they are introduced into the mass analysis device 34. The data produced by the gas chromatograph 32 and mass analysis device 34 are typically collected by a data analysis apparatus 46 and stored in a computerized data file for computer analysis using commercially available software known to the art. This configuration also is not limited solely to the gas chromatographs 32 and mass analysis devices 34 mentioned above. Other detection and analysis methods and devices, such as those mentioned above, may be configured in a similar manner depending on the application and the data required.

Another embodiment of the invention is shown in FIG. 5. In that embodiment, a condensation trap 40 is interposed between a mouthpiece 42 and the entrance conduit 14 of a collection chamber 12. The condensation trap 40 preferably is made of a non-reactive material, such as glass, that is loosely packed with a non-reactive, non-adsorbent material 44 such as glass wool, glass beads or other such materials having a relatively large surface area and which will not hinder the flow of air through the trap. The glass packing 44 preferably is arranged to present a maximum surface area, without unduly restricting the flow of a breath sample from the subject. The outer diameter of the condensation trap 40 is preferably about 0.236 inches (0.60 centimeters), but may be varied depending on the subject and the particular test conditions. In addition, the shape and placement of the glass packing 44 also may be altered to meet the requirements of a particular subject and the study conditions.

The condensation trap 40 is preferably connected to the entrance conduit 14 with the thumb screw and ferrule connection 14c that corresponds to the entrance union 14b discussed above. In the preferred embodiment, the condensation trap 40 is maintained at ambient room temperatures, or if appropriate, somewhat cooler temperatures. Thus, when the subject's breath sample passes through the condensation trap 40, the relatively non-volatile components, as well as relatively minor amounts of the volatile components, in the breath sample condense on the glass packing 44 and on the interior surfaces of the trap 40. The uncondensed volatile components of the breath sample are permitted to continue through the condensation trap 40 into the collection chamber 12 for further analysis. The condensation trap 40 may then be treated to remove the components and materials condensed on the trap 40 using the thermal desorber 36 discussed above, although other methods of removing the components from the trap may be used as well. The collected components are then measured and analyzed using the gas chromatograph 32 and mass spectrometer 34 discussed above or other appropriate equipment as mentioned above. The volatile components that pass through the condensation trap 40 are retained in the collection chamber 12 and are collected using the adsorbent trap 30 and procedures discussed above.

A typical example of the use of the apparatus and method of invention includes supplying a human subject with a predetermined amount of a food product for oral processing, typically about three grams, although more or less may be used depending on the particular product and circumstances. The subject is instructed to inhale and then chew the product for a period of time with nose and mouth sealed, preferably about 2–20 seconds. At the end of the time period, the subject is instructed to exhale a breath sample from his or her mouth through a mouthpiece 24 into a collection chamber 12 for a period of time, preferably about 3–10 seconds.

It is important that the volume of exhaled breath be less than the volume of the collection chamber to avoid loss of volatiles and relatively non-volatiles. The volume of the breath sample is preferably about 265 to 400 milliliters, and most preferably about 200 to 250 millimeters.

Prior to the test period, the subject may be instructed to practice exhaling into the collection chamber 12 to determine the degree of effort needed to provide a breath sample of that size, working with a flow meter or a balloon-type device which can control the volume of air which can be easily exhaled. If the breath sample is to be exhaled for 2–7 seconds, the balloon-type device is preferred. Alternatively, if the breath sample is to be exhaled for more than 7 seconds, then a flow meter may be temporarily attached to the entrance or exit conduits 14 or 16 of the chambers 12 during the procedure to monitor the flow of air actually displaced from the collection chambers 12 (and thus the volume of the breath sample).

Once the breath sample is collected and exhalation is complete, an adsorbent trap 30 is connected to the entrance conduit 14 (or the exit conduit 16) of the collection chamber 12 containing the first breath sample. As described above, a non-reactive gas source 28, such as helium, is connected to the exit conduit 16 (or the entrance conduit 14) of the collection chamber 12. A sufficient amount of gas is supplied to the collection chamber 12 to purge the chamber of the breath sample, through the adsorbent trap 30. In the preferred embodiment, the gas source 28 is connected to the exit conduit 16 as soon as possible after the breath sample is collected and exhalation is complete. A gas flow of about 135 milliliters per minute is maintained for about 18 minutes. The trap 30 is then sealed, labeled and put aside for subsequent analysis and measurement of the released components captured from the breath sample.

If multiple breath samples are desired, then the subject is instructed to inhale and chew the product sample for a similar period of time with nose and mouth sealed. Once the subject has completed chewing the product sample for a first period of time, the subject is instructed to exhale into a first collection chamber 12. The subject is instructed to inhale, chew again for a second period of time and exhale into a second collection chamber 12. This procedure is repeated until a sufficient number of breath samples have been obtained to characterize the release profiles of the sample over a representative period of time. Each breath sample is then separately purged from the collection chambers 12 into separate adsorbent traps 30 connected to the collection chambers 12.

Next, each of the adsorbent traps 30 is introduced separately into the thermal desorber 36 so that any volatile or relatively non-volatile components released by the product samples and collected in the traps 30 may be analyzed and measured by the gas chromatograph 32 and mass analysis device 34 as discussed above. The results of that analysis may then be used to change the product formula or preparation process, or as data for further studies.

The collection of relatively non-volatile components using a condensation trap 40 follows a similar procedure. In one application, the subject is instructed to orally process a predetermined amount of a sample and to exhale through a condensation trap 40 connected to a collection chamber 12, as mentioned above. The condensation trap 40 is then removed from the entrance conduit 14 of the collection chamber 12, so that the volatile components present in the collection chamber 12 may be purged into an adsorbent trap 30, for desorption and analysis as mentioned above. The condensation trap 40 is then connected to a thermal desorber 36 for revaporization of the relatively non-volatile and volatile components collected by the condensation trap 40. These components are measured and analyzed using the gas chromatograph 32 and mass analysis device 34 as described above. To the extent necessary, suitable measures known in the art may be taken to remove or otherwise compensate for any water vapor collected on the condensation trap 40. This may include steps such as dry purging.

The apparatus and method of the invention is further illustrated in the following examples:

EXAMPLE 1

A subject was given a mouthful (approximately 4–5 grams) of a commercially available carbonated, cola flavored beverage. The sample was circulated through the subject's mouth for several seconds, and then swallowed. The subject then exhaled rapidly for about 3 seconds through an about 1–3 inch (2.54–7.63 centimeter) by 0.125 inch (0.318 centimeter) outer diameter nylon tube into a glass collection chamber, as described above, that was maintained at about 85° C. in a temperature controlled cabinet. After the sample was collected, a Tenax adsorptive trap packed with about 90 milligrams of Tenax-TA was attached to the entrance conduit of the collection chamber. A non-reactive gas source was attached to the exit conduit of the chamber. The contents of the collection chamber were purged into the adsorptive trap with the non-reactive gas, as discussed above, for about 20 minutes with a gas flow of about 135 milliliters/minute.

The adsorptive trap was then placed in a Chrompack purge and trap injector operated in the thermal desorption mode, and arranged to feed desorbed materials into a Varian 3400 Gas Chromatograph, as mentioned above. In the desorber, a liquid nitrogen cold trap was cooled to about −140° C. for about 4 minutes. Then, the adsorbent trap was heated to about 220° C. as helium gas was allowed to flow through the adsorptive trap, at a flow rate of about 14 milliliters/minute for about 12 minutes to elute the captured volatiles and relatively non-volatiles from the adsorptive trap into the cold trap. The liquid nitrogen flow to the cold trap was then shut off and the trap was ballistically heated to about 180° C. to quickly transfer the volatiles onto the Varian 3400 Gas Chromatograph which was further connected to a Finnigan ITS40 Ion Trap Detector, as mentioned above.

The volatiles and relatively non-volatile components captured from the breath sample were separated by the gas chromatograph on a 25 meter by 0.2 millimeter inner diameter DB-1 capillary column having a 0.5 micron film thickness. The column head pressure was about 12.5 psi, and the following column temperature programming was used: initial temperature was about 40° C. for about 3 minutes; then, the column temperature was increased to about 140° C. at a rate of about 4° C./minute; the column temperature was further increased to about 220° C. at a rate of about 8° C./minute; and then the final temperature of about 220° C. was held for 20 minutes.

Figure 6:
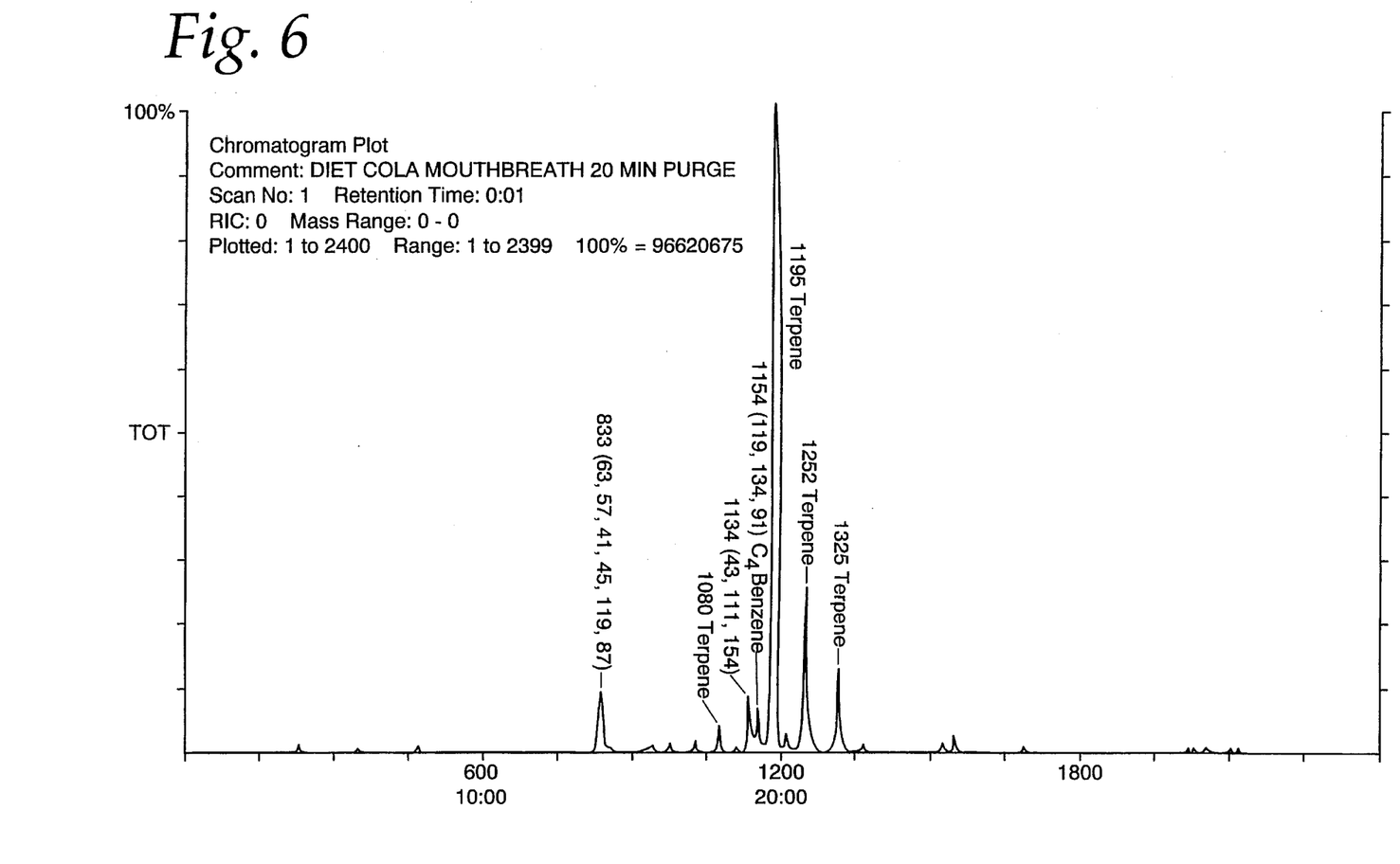
FIG. 6 is a Plot of an ITS40 ion trap detector analysis as performed in Example 1 (scans 1–2400).

Each separated component eluted off the gas chromatographic column was introduced into the ITS40 ion trap operating in the EI mode and using autoionization control. Masses from 35 to 300 atomic mass units were scanned at a rate of 1 scan per second. The peak threshold was set to 10 counts, mass effect to 100 mmu/100 amu, and background mass to 34 amu. The results of the scan are shown in FIG. 6.

EXAMPLE 2

A three gram sample of a commercially available vanilla ice cream product was placed in the mouth of a subject and chewed for about 10 seconds with the subject's mouth and nose closed. The subject then exhaled through a 1 inch (2.54 centimeters) by 0.25 inch (0.64 centimeter) outer diameter glass tube into a glass collection chamber, as discussed above, maintained at a temperature of about 125° C. in a temperature controlled cabinet. A Tenax adsorption trap and a non-reactive gas source were attached to the collection chamber as in Example 1. The chamber was purged into the adsorptive trap for about 21 minutes at a gas flow rate of about 135 milliliters/minute to transfer the volatiles and relatively non-volatiles into the adsorptive trap.

As in Example 1, the adsorptive trap was placed in a Chrompack purge and trap injector, operated in the thermal desorption mode, and was connected to a Varian 3400 Gas Chromatograph and Finnigan ITS40 Ion Trap Detector. The volatiles and relatively non-volatiles captured from the breath sample were desorbed from the trap and introduced into the gas chromatograph, as in Example 1.

The volatiles and relatively non-volatiles were separated by the gas chromatograph on a 25 meter by 0.2 millimeter inner diameter DB-1 capillary column with a 0.5 micron film thickness and at a column head pressure of about 12.5 psi. The following column temperature programming was used: the initial temperature was about −10° C. for about 3 minutes; then, the column temperature was increased at about 15° C./minute to about 40° C. and held there for about 3 minutes; the column temperature was further increased to about 140° C. at a rate of about 4° C./minute; the column temperature was again increased to about 220° C. at a rate of about 8° C./minute and held at that final temperature for about 20 minutes.

Figure 7:
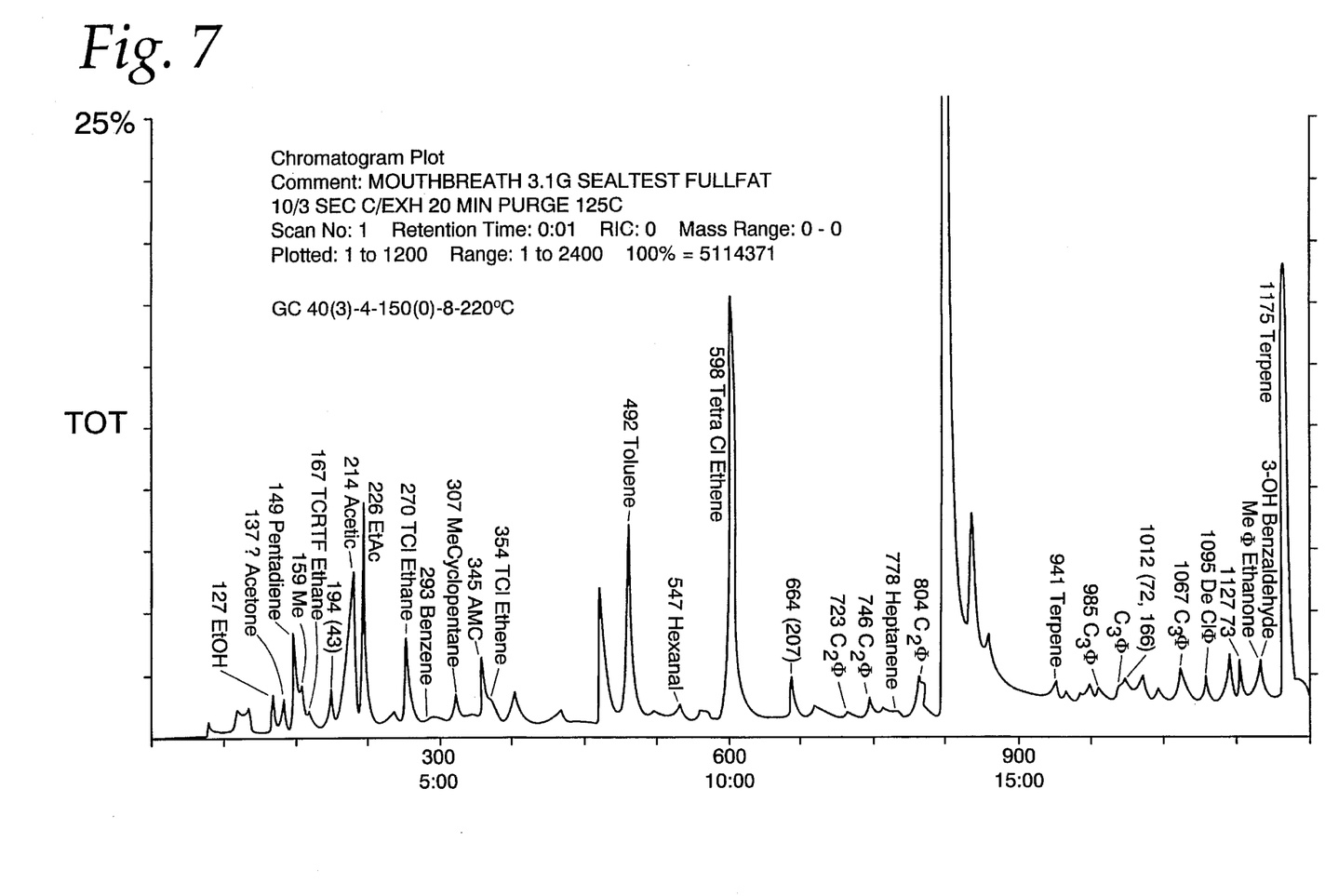
FIG. 7 is a Plot of an ITS40 ion trap detector analysis as performed in Example 2 (scans 1–1200).
Figure 8:
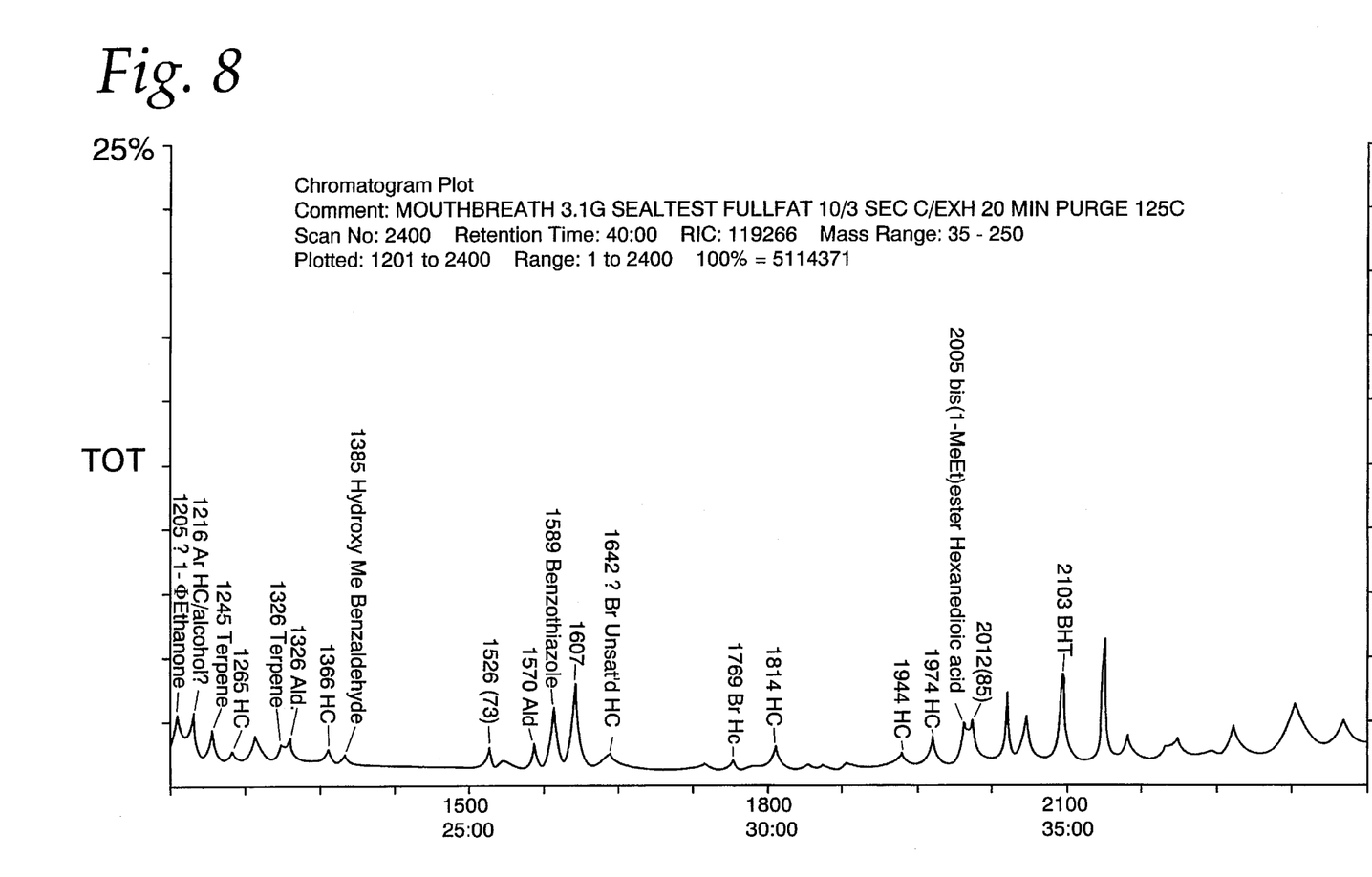
FIG. 8 is a Plot of an ITS40 ion trap detector analysis as performed in Example 2 (scans 1201–2400).

The components eluted off the gas chromatographic column were introduced into the ITS40 Ion Trap, which was operated as mentioned in Example 1. The results of the ion trap scan are shown in FIGS. 7 and 8.

EXAMPLE 3

A commercially available mayonnaise product and an unflavored reduced fat (1.45% fat) mayonnaise base similar in composition to commercially available reduced fat mayonnaise products were spiked with a mixture of ethyl esters and methyl n-alkyl ketones so that each compound was present at a level of about 0.1 ppm. Samples were stored at room temperature in a screw cap plastic jar.

In this example, 5 cycles of chewing, exhaling and inhaling were carried out using samples of each spiked mayonnaise product. The exhaled breaths from cycles 1, 3 and 5 were collected in separate glass collection cylinders. The exhaled breaths from cycles 2 and 4 were passed directly to the atmosphere and were not collected. Care was taken to minimize swallowing of sample during the 5 cycles.

For each trial, about 3 grams of one of the spiked mayonnaise products was placed in the subject's mouth and chewed for about 5 seconds. Then, the subject exhaled for about 3 seconds through a 1 inch (2.54 centimeter)×0.25 inch (0.64 centimeter) outer diameter glass mouthpiece into a first glass collection chamber (Cycle 1). After the subject inhaled through his nose for about 2 seconds, the sample was chewed for about an additional 5 seconds. The subject then exhaled through another 1 inch (2.54 centimeter)×0.25 inch (0.64 centimeter) outer diameter mouthpiece into the atmosphere (Cycle 2).

In the third cycle, the above procedure was followed and the breath sample was exhaled into a second collection chamber. A fourth cycle was completed by exhaling the breath sample into the atmosphere. A fifth cycle was completed by exhaling the breath sample into a third collection chamber. The collection chambers were held in a temperature controlled cabinet at about 85° C.

Upon completion of the fifth cycle, Tenax adsorptive traps and non-reactive gas sources were attached to the collection chambers as described in Examples 1 and 2. The collection chambers were purged for about 18 minutes at about 130 milliliters/minute to transfer the breath samples into the adsorptive traps.

Each adsorptive trap was then placed into a Chrompack purge and trap injector operated in the thermal desorption mode as described in Example 1. The desorber was connected to a Hewlett-Packard 5890 Gas Chromatograph which was arranged to feed into a Hewlett-Packard 5971A Mass Spectrometer The desorbed volatiles and relatively non-volatiles from each breath sample were separated by the gas chromatograph on a 30 meter by 0.25 millimeter inner diameter DB-5 capillary column at a column head pressure of about 9.5 psi. The following temperature programming was used: the initial temperature was held at about 40° C. for about 3 minutes; then the column temperature was increased to about 140° C. at a rate of about 4° C./minute; and column temperature was further increased to about 220° C. at a rate of about 8° C./minute. This final temperature was held for about 20 minutes.

The components eluted off the gas chromatograph were introduced into the Hewlett-Packard 5971A Mass Spectrometer which was set in a selected ion monitoring mode. The ions monitored were chosen to give good selectivity and sensitivity for the compounds of interest as shown on the table below:

| SELECTED ION MONITORING OF TEST MIXES | |
|---|---|
| Compounds | Ions Monitored |
| 2-Butanone | 72 |
| 2-Pentanone, ethyl propionate | 58, 57 |
| Other ketones + ethyl esters | 58, 88 |

Maximum 2 ions per group. Dwell time set to give 2 scans/second. Electron multiplier voltage set to autotune value plus 400 volts.

The following ions were detected with the indicated peak areas:

TABLE 1

Mass Spectrometer Results For Reduced Fat (1.45%) Mayonnaise Base With 0.1 ppm K + EE (mixture of ketones and ethyl esters) Added

| | Retention | Peak Areas × 10³ | | |
|---|---|---|---|---|
| | Time (min) | Cycle 1 | Cycle 3 | Cycle 5 |
| 2-Butanone | 2.32 | 10,894 | 7,943 | 5,487 |
| 2-Pentanone | 3.24 | 4,406 | 2,068 | 1,347 |
| 2-Hexanone | 5.37 | 25,103 | 10,659 | 5,470 |
| 2-Heptanone | 8.68 | 37,532 | 17,728 | 10,428 |
| 2-Octanone | 12.60 | 29,601 | 18,693 | 14,731 |
| 2-Nonanone | 16.64 | 15,416 | 13,893 | 15,756 |
| 2-Decanone | 20.54 | 4,896 | 5,095 | 7,035 |
| 2-Undecanone | 24.25 | 2,019 | 2,101 | 2,419 |
| Ethyl Propionate | 3.64 | 37,874 | 11,194 | 4,191 |
| Ethyl Butyrate | 5.74 | 15,670 | 4,735 | 1,501 |
| Ethyl Pentanoate | 9.11 | 23,773 | 9,571 | 4,082 |
| Ethyl Hexanoate | 12.99 | 16,088 | 9,358 | 6,569 |
| Ethyl Heptanoate | 16.92 | 10,108 | 7,290 | 7,412 |
| Ethyl Octanoate | 20.74 | 4,799 | 3,551 | 3,737 |
| Ethyl Nonanoate | 24.36 | 2,087 | 1,614 | 1,200 |

TABLE 2

Mass Spectrometer Results For Full Fat Mayonnaise With 0.1 ppm K + EE (mixture of ketones and ethyl esters)

| | Retention | Peak Areas × 10³ | | |
|---|---|---|---|---|
| | Time (min) | Cycle 1 | Cycle 3 | Cycle 5 |
| 2-Butanone | 2.32 | 17,477 | 8,588 | 4,855 |
| 2-Pentanone | 3.24 | 5,075 | 2,081 | 1,278 |
| 2-Hexanone | 5.37 | 12,116 | 8,585 | 5,509 |
| 2-Heptanone | 8.68 | 9,917 | 8,308 | 6,918 |
| 2-Octanone | 12.60 | 4,628 | 4,155 | 4,668 |
| 2-Nonanone | 16.64 | 2,161 | 1,896 | 2,521 |
| 2-Decanone | 20.54 | 633 | 932 | 815 |
| 2-Undecanone | 24.25 | 1,001 | 739 | 299 |
| Ethyl Propionate | 3.64 | 33,468 | 16,681 | 7,699 |
| Ethyl Butyrate | 5.74 | 8,974 | 5,382 | 3,062 |
| Ethyl Pentanoate | 9.11 | 9,465 | 5,464 | 4,091 |
| Ethyl Hexanoate | 12.99 | 3,676 | 2,928 | 2,922 |
| Ethyl Heptanoate | 16.92 | 2,012 | 1,879 | 2,111 |
| Ethyl Octanoate | 20.74 | 770 | 1,019 | 987 |
| Ethyl Nonanoate | 24.36 | 832 | 564 | 233 |

Thus, by measuring and analyzing successive breath samples taken at predetermined intervals, the apparatus and method of the invention will provide data on the release of volatile and relatively non-volatile components from orally processed food products over time. This is helpful in identifying and analytically studying food products which produce a high flavor impact upon initial chewing of the product, and exhibit a substantial loss of flavor prior to swallowing.

Products which do not exhibit a substantial loss of flavor prior to swallowing may also be studied with objective data on the content and nature of components released by such products. In addition, by continuing to take breath samples after swallowing of a food product, the "after-taste" or residual released volatiles and relatively non-volatiles may be analyzed using the apparatus and method of the invention.

Hence, the invention permits the study and analysis of components released from food or other products that are orally processed. The apparatus and method of the invention permits the objective and analytical study of the flavor characteristics of food and other orally processed matter resulting in greater sensitivity, a larger range of detected compounds and a greater selectivity than previously permitted by the prior art. Moreover, the above examples and disclosures should not be considered as limiting the invention to that particular subject matter. The invention may be adapted for the study of other appropriate compositions which may be carried in the breath of a subject.

Similarly, while the invention has been described by reference to certain specific descriptions and examples which illustrate preferred materials, configurations and conditions, including those pertaining to the processing of food products, it is understood that the invention is not limited thereto. Rather, all alternatives, modifications and equivalents within the scope and spirit of the invention so described are considered to be within the scope of the appended claims.

What is claimed is:

1. A method for collecting, analyzing, and measuring a plurality of volatile and relatively non-volatile components that are released upon oral processing of solid matter, semi-solid matter, liquid matter or combinations thereof transportable in a breath of a subject comprising:

providing a predetermined amount of solid matter, semi-solid matter, liquid matter or combinations thereof to the subject for orally processing;

oral processing of the matter by the subject in a way so that the matter is physically altered by oral processing for a predetermined period of time sufficient to release volatile and relatively non-volatile components from the matter into an oral cavity;

obtaining from the subject at least one sample of breath containing volatile and relatively non-volatile components released from the orally processed matter, each breath sample flowing into one of a plurality of collection chambers maintained at a constant temperature and volume;

directing each breath sample from each one of a plurality of the collection chambers through at least one separation interface, the interface disposed to capture thereon the released volatile and relatively non-volatile components from the breath sample; and transferring simultaneously both the released volatile and the released relatively non-volatile components from the separation interface into an apparatus for analyzing and measuring the released components.

2. The method of claim 1 wherein the subject is a human and the matter is orally processed by chewing.

3. The method of claim 1 wherein each breath sample is obtained by flowing the sample into a separate collection chamber maintained under controlled temperature and volume conditions.

4. The method of claim 3 wherein a separation interface is provided for each breath sample, the separation interface is disposed within a non-reactive housing operatively connected to the collection chamber containing the breath sample, and the breath sample is directed through the separation interface by flowing the sample from the collection chamber through the non-reactive housing.

5. The method of claim 4 wherein the released volatile and relatively non-volatile components are separated and captured from the breath sample by adsorption on the surface of the separation interface.

6. The method of claim 5 wherein the released volatile and relatively non-volatile components are purged from the separation interface by thermal desorption and are introduced into the analyzing and measuring apparatus by a flow of non-reactive gas.

7. The method of claim 3 wherein relatively non-volatile components released from the orally processed matter are captured from the breath sample by flowing the breath sample through a first condensation interface maintained at a temperature such that the relatively non-volatile components in the breath sample condense on the first interface as the breath sample flows through the first interface into a collection chamber and thereafter onto a second interface, wherein the volatile components are captured.

8. The method of claim 7 wherein the relatively non-volatile components are purged from the first condensation interface and introduced into the measuring and analyzing apparatus by revaporizing the relatively non-volatile components from the first condensation interface and flowing the relatively non-volatile components into the analyzing and measuring apparatus with a non-reactive gas.

9. The method of claim 1 comprising measuring and analyzing the volatile and relatively non-volatile components by separating the components and measuring their amounts using gas chromatography.

10. The method of claim 9 comprising introducing each volatile and relatively non-volatile component separated by gas chromatography into a device for the spectroscopic identification and measurement of each such component.

11. The method of claim 10 comprising identifying and measuring the volatile and relatively non-volatile components wherein the spectroscopic identification and measurement includes a mass analysis of the components.

12. The method of claim 11 comprising identifying and measuring the volatile and relatively non-volatile components wherein the mass analysis is with a mass spectrometer.

13. The method of claim 11 comprising identifying and measuring the volatile and relatively non-volatile components wherein the mass analysis device is an ion trap detector.

14. The method of claim 1 wherein the volatile and relatively non-volatile components are separated and measured by liquid chromatography.

15. A method for collecting, analyzing, and measuring a plurality of volatile and relatively non-volatile components released from solid matter, semi-solid matter, liquid matter or combinations thereof orally processed by a human subject comprising:

providing to a human subject for oral processing a predetermined amount of solid matter, semi-solid matter, liquid matter or combinations thereof;

chewing of the matter by the subject for a predetermined period of time in a way so that the matter is physically altered by oral processing sufficient to release volatile and relatively non-volatile components into the subject's oral cavity;

obtaining from the subject a plurality of breath samples containing volatile and relatively non-volatile components released from the orally processed matter at preselected intervals of time by flowing each successive breath sample into a different one of a corresponding plurality of collection chambers;

holding each breath sample in each collection chamber under controlled temperature and volume conditions;

evacuating each breath sample from each collection chamber into a corresponding separation chamber provided with an adsorptive interface, the interface disposed to capture thereon simultaneously the released volatile and relatively non-volatile components from each breath sample; and purging the volatile and relatively non-volatile components simultaneously from the adsorptive interface into an apparatus for analyzing and measuring the released components.

16. An apparatus for collecting, analyzing, and measuring a plurality of volatile and relatively non-volatile components released into the breath of a subject by orally processing solid matter, semi-solid matter, liquid matter or combinations thereof comprising:

a mouthpiece sized and positionable to receive a breath sample from the subject;

the mouthpiece operatively connected to one of a plurality of collection chambers sized to collect and retain the breath sample within each chamber, the chamber provided with a separation interface disposed to capture thereon volatile and relatively non-volatile components released into the breath sample from the orally processed matter; and an extraction station and an apparatus with device for analyzing and measuring the released volatile and relatively non-volatile components, the extraction station disposed to receive the separation interface therein, purge simultaneously the captured volatile and relatively non-volatile components from the separation interface, and introduce the volatile and relatively non-volatile components into the analyzing and measuring device.

17. The apparatus of claim 16 wherein the mouthpiece is operatively connected to at least one first chamber for receiving the breath sample that is maintained under controlled volume and temperature conditions; the first collection chamber operatively connected to at least one second chamber provided with the separation interface; the first collection chamber further provided with a connection union disposed to receive a non-reactive gas source for evacuating the breath sample from the first collection chamber into the second chamber.

18. The apparatus of claim 17 wherein the measuring and analyzing device comprises a gas chromatograph for separating and measuring the captured volatile and relatively non-volatile components.

19. The apparatus of claim 18 wherein the measuring and analyzing device comprises a gas chromatograph operatively connected to a spectroscopic analysis device.

20. The apparatus of claim 19 wherein the spectroscopic analysis device is a mass analysis device.

21. The apparatus of claim 17 wherein the separation interface is a substrate provided with an exposed, adsorptive surface disposed to capture thereon the volatile and relatively non-volatile components from the breath sample.

22. The apparatus of claim 16 wherein the mouthpiece is operatively connected to a first condensation trap; the first trap provided with a condensation interface disposed to capture thereon at least relatively non-volatile components released into the breath sample by orally processed matter; the condensation trap operatively connected to the collection chamber into which the relatively volatile components flow and pass the condensation trap; thereafter the collection chamber is operatively connected to a second separation interface, disposed to capture thereon volatile components released into the breath sample which have flowed past the first condensation trap.

23. The apparatus of claim 22 wherein the extraction station is disposed to receive the first condensation trap therein and to purge the collected volatile and relatively non-volatile components into the analyzing and measuring apparatus.

24. An apparatus for collecting, analyzing, and measuring a plurality of volatile and relatively non-volatile components released into the breath of a subject by the oral mastication of solid matter, semi-solid matter, liquid matter, or combinations thereof by a human subject comprising:

a plurality of collection chambers for receiving breath samples, each collection chamber provided with a mouth piece disposed to flow a breath sample from the subject's mouth into the collection chamber and a releasable coupling to a source of non-reactive gas with the flow rate sufficient to purge the breath sample from the collection chamber in a predetermined period of time;

a separation chamber releasably coupled to anyone of the plurality of collection chambers and disposed to receive the breath sample purged from the collection chamber; the separation chamber provided with an adsorption interface disposed to capture thereon volatile and relatively non-volatile components carried in the breath sample;

a device for analyzing and measuring the released components; and an extraction station operatively coupled to the analyzing and measuring device, the extraction station provided with a thermal desorber disposed to receive the separation chamber therein and to remove in one step the volatile and relatively non-volatile components from the adsorptive interface; and a non-reactive gas source with a flow rate sufficient to introduce the volatile and relatively non-volatile components into the analyzing and measuring device.

25. The apparatus of claim 24 where the analyzing and measuring device comprises a gas chromatograph operatively connected to a spectroscopic analysis device.

26. An apparatus for collecting, analyzing, and measuring a plurality of volatile and relatively non-volatile components released into the breath of a subject by orally processing solid matter, semi-solid matter, liquid matter or combinations thereof, said apparatus comprising:

means for providing a predetermined amount of solid matter, semi-solid matter, liquid matter or combinations thereof to the subject for orally processing;

means for oral processing of the matter by the subject in a way so that the matter is altered by saliva and breath for a predetermined period of time sufficient to release volatile and relatively non-volatile components from the matter into an oral cavity;

means for obtaining from the subject at least one sample of breath containing volatile and relatively non-volatile components released from the orally processed matter, each breath sample flowing into one of a plurality of collection chambers maintained at a constant temperature and volume;

means for directing each breath sample from the collection chamber through at least one separation interface, the interface disposed to capture thereon the released volatile and relatively non-volatile components from the breath sample; and means for transferring simultaneously both the released volatile and the released relatively non-volatile components from at least one separation interface into an apparatus for analyzing and measuring the released components.

* * * * *